US011559220B2

(12) United States Patent
Ha et al.

(10) Patent No.: US 11,559,220 B2
(45) Date of Patent: Jan. 24, 2023

(54) MEASUREMENT UNIT FOR MEASURING A BIO-IMPEDANCE

(71) Applicants: IMEC VZW, Leuven (BE); STICHTING IMEC NEDERLAND, Eindhoven (NL)

(72) Inventors: Hyunsoo Ha, Leuven (BE); Nick Van Helleputte, Leuven (BE)

(73) Assignees: IMEC VZW, Leuven (BE); STICHTING IMEC NEDERLAND, Eindhoven (NL)

( * ) Notice: Subject to any disclaimer, the term of this patent is extended or adjusted under 35 U.S.C. 154(b) by 423 days.

(21) Appl. No.: 16/784,235

(22) Filed: Feb. 6, 2020

(65) Prior Publication Data

US 2020/0253500 A1 Aug. 13, 2020

(30) Foreign Application Priority Data

Feb. 7, 2019 (EP) ..................................... 19156041

(51) Int. Cl.
*A61B 5/053* (2021.01)
*A61B 5/0245* (2006.01)
(Continued)

(52) U.S. Cl.
CPC ............ *A61B 5/053* (2013.01); *A61B 5/0245* (2013.01); *A61B 5/0809* (2013.01); *A61B 5/681* (2013.01); *A61B 5/7225* (2013.01); *A61B 5/7278* (2013.01)

(58) Field of Classification Search
CPC ..... A61B 5/053; A61B 5/0245; A61B 5/0809; A61B 5/681; A61B 5/7225; A61B 5/7278
See application file for complete search history.

(56) References Cited

U.S. PATENT DOCUMENTS 8,179,195 B1  5/2012 Huijsing et al.
9,615,744 B2  4/2017 Denison et al.
(Continued)

OTHER PUBLICATIONS

Hyunsoo, A Bio-Ipedance Readout IC with Frequency Sweeping from 1k to 1 MHz for Electrical Impedance Tomography, 2017 Symposium on VLSI Circuits Digest of Technical Papers (Year: 2017).*

(Continued)

*Primary Examiner* — Unsu Jung
*Assistant Examiner* — Roland Dinga
(74) *Attorney, Agent, or Firm* — Moser Taboada (57) ABSTRACT

A measurement unit for measuring a bio-impedance of a body, the measurement unit comprising a current generator circuit, a readout circuit, and a baseline cancellation current circuit,
  wherein the current generator circuit is configured to amplify a reference current to form a measurement current to be driven through a body to generate a measurement voltage representing the bio-impedance;
  wherein the readout circuit comprises a Instrumentation amplifier (IA) which has a transconductance stage and a transimpedance stage, wherein the IA is configured to:
    produce a first current in the transconductance stage, the first current being proportional to the measurement voltage,
    receive a second current from the baseline cancellation current circuit,
    produce an output voltage in the transimpedance stage, the output voltage being proportional to a difference between the first current and the second current and representative of the measured bio-impedance;
  wherein the baseline cancellation current circuit is configured to amplify the reference current by a factor to form the second current and deliver it to the IA,
  wherein the factor is such that that the absolute value of the difference between the first and the second current is below a threshold such that a baseline of the first current is cancelled by the second current.

15 Claims, 9 Drawing Sheets

(51) Int. Cl.
  *A61B 5/08* (2006.01)
  *A61B 5/00* (2006.01)

(56) References Cited

U.S. PATENT DOCUMENTS

| | | |
|---|---|---|
| 2014/0077873 A1 | 3/2014 | Motz et al. |
| 2016/0074674 A1 | 3/2016 | Kohli et al. |
| 2016/0294331 A1 | 10/2016 | Ivanov |
| 2017/0071552 A1* | 3/2017 | Harpe ................. A61B 5/30 |
| 2019/0274579 A1* | 9/2019 | Lee ................. A61B 5/6824 |

OTHER PUBLICATIONS

Chen et al., "A CMOS Enhanced Solid-State Nanopore Based Single Molecule Detection Platform", 35th Annual International Conference of the IEEE EMBS Osaka, Japan, Jul. 3-7, 2013.

Ko et al., "Ultralow-Power Bioimpedance IC With Intermediate Frequency Shift Chopper", IEEE Transactions on Circuits and Systems—II: Express Briefs, vol. 63, No. 3, Mar. 2016.

Kim et al., "A 1.4mΩ—Sensitivity 94dB-Dynamic-Range Electrical Impedance Tomography SoC and 48-Channel Hub SoC for 3D Lung Ventilation Monitoring System", Smart SoCs For Innovative Applications, Digest of Technical Papers, 2017 IEEE International Solid-State Circuits Conference, pp. 354-356, Feb. 8, 2017.

Ha et al., "Measurement and Analysis of Input-Signal Dependent Flicker Noise Modulation in Chopper Stabilized Instrumentation Amplifier", IEEE Solid-State Circuits Letters, vol. 1, No. 4, pp. 90-93, Apr. 2018.

\* cited by examiner

MEASUREMENT UNIT FOR MEASURING A BIO-IMPEDANCE

CROSS-REFERENCE TO RELATED APPLICATION

The present application claims the benefit of the European Patent Application No. 19156041.6, filed on Feb. 7, 2019, the contents of which are incorporated herein by reference

TECHNICAL FIELD

The present invention relates generally to biosignal measurement devices comprising units for measuring bio-impedance signals and, more particularly, to units for measuring time varying bio-impedance signals.

BACKGROUND

Bio-impedance measurements are commonly used to measure the composition of body tissue as well as the movement of the body tissue or the movement of fluids or gases within the body tissue. An electrode pair is typically attached to the skin of the body and a known current is driven through the body from one electrode to the other. Due to the impedance of the body, the bio-impedance, a measurable voltage is created as the current runs through the body. The bio-impedance can thus be derived from the measured voltage and the known current.

The measured bio-impedance has a time invariant part, corresponding to the impedance of the body tissue when it is still. The measured bio-impedance may furthermore have a time varying part superimposed on the time invariant part, wherein the time varying part corresponds to the movement of the body tissue and/or the movement of fluids or gases within the body tissue.

The bio-impedance measurement may be conducted using the same electrode pair for driving the current through the body as for measuring the voltage, i.e. a 2-electrode setup. However, to improve the accuracy a 4-electrode setup is often used. Herein one pair of electrodes is used to drive the current and a second pair of electrodes is used to measure the voltage. As no current runs through the second pair of electrodes no voltage drop is generated at the electrode-tissue interface which improves the accuracy of the voltage measurement.

SUMMARY

It is an object of the invention to improve on existing bio-impedance measurement units. In particular, it is an object to provide bio-impedance measurement units having a high accuracy and being inexpensive.

These and other objects of the invention are at least partly met by the invention as defined in the independent claims. Preferred embodiments are set out in the dependent claims.

According to an embodiment, there is provided a measurement unit for measuring a bio-impedance of a body, the measurement unit comprising a current generator circuit, a readout circuit, and a baseline cancellation current circuit, wherein the current generator circuit is configured to amplify a reference current to form a measurement current to be driven through a body tissue of the body, such that a measurement voltage is generated, the measurement voltage depending on the measurement current and the bio-impedance of the body;

wherein the readout circuit comprises an Instrumentation Amplifier (IA) which has a transconductance stage and a transimpedance stage, wherein the IA is configured to:
produce a first current in the transconductance stage, the first current being proportional to the measurement voltage,
receive a second current from the baseline cancellation current circuit,
produce an output voltage in the transimpedance stage, the output voltage being proportional to a difference between the first current and the second current and representative of the measured bio-impedance;

wherein the baseline cancellation current circuit is configured to amplify the reference current by a factor to form the second current and deliver it to the IA,
wherein the factor is such that that the absolute value of the difference between the first and the second current is below a threshold during the measurement of the bio-impedance, such that a baseline of the first current is cancelled by the second current.

The measurement unit may provide a high accuracy of the measurement as noise originating from the reference current may be reduced. It is an insight of the invention that the time variant part of the bio-impedance between two electrodes, the part that changes with time, may contain very important information regarding e.g. heartrate, respiration etc. However, the time variant part of the bio-impedance may be very small in comparison to the time invariant part. For example, heart beats may give rise to a 10 mΩ undulation superimposed on a 1 kΩ static body impedance. It is a further insight that noise in the reference current may propagate through the measurement and give rise to corresponding noise in the measured impedance. If the time variant part of the bio-impedance is small in comparison to the total bio-impedance, i.e. the sum of the time invariant and the time variant part, then the time invariant part of the bio-impedance may be partly or fully obscured by the noise.

In a bio-impedance measurement the measurement voltage may be seen as a representative of the total bio-impedance between two electrodes, i.e. the sum of the time invariant and the time variant part. The measurement voltage may be proportional to the measurement current which in turn is proportional to the reference current. The measurement voltage may also be proportional to the total bio-impedance.

Conventionally, the measurement voltage may be amplified to form the output voltage which may then also be seen as representative of the total bio-impedance. The output voltage signal may e.g. be converted, taking into account all proportionality constants for forming an output voltage based on the reference current, to a total bio-impedance signal as a function of time. The conversion may be done by a measurement unit or by another device which receives the output voltage signal from the measurement unit. It is an insight of the invention that in such a conventional device the output voltage signal may never have a better signal to noise ratio (SNR) than the reference current, as the output voltage is proportional to the reference current. For example, if the reference current has a SNR of 1000, corresponding to 0.1% noise, then the noise of a 1 mΩ static body impedance would be 1Ω. This would e.g. obscure a 10 mΩ undulation superimposed on a 1 mΩ static body impedance.

It is an insight of the invention that it may be possible to measure a part of the total bio-impedance, e.g. the time variant part or the time variant part plus some of the time invariant part, and that it may be possible to ensure that noise of the measured part of the bio-impedance is smaller than the noise would be if the total bio-impedance had been measured. In the following examples, the inventive concept is exemplified under the conditions that a nominally constant measurement current, with the exception of noise, is applied and that no other noise sources than the noise of the reference current exists. In light of this application it will be apparent to the skilled person how to modify the examples to account for e.g. a modulated measurement current or other noise sources.

The measurement unit may be configured such that the measurement voltage is converted to a first current in the transconductance stage. Thus the first current may be seen as representative of the total bio-impedance. By taking the difference between the first current and the second current it may be possible to form a representative of a part of the bio-impedance. If the second current is derived from the reference current, just as the first current is, the noise in the first and second current may be correlated. Thus, as a baseline of the first current is cancelled by the second current the corresponding noise may simultaneously be cancelled. The difference between the first and the second current may then be passed to the transimpedance stage and again converted to an output voltage. The output voltage in the transimpedance stage may then also be seen as a representative of a part of the bio-impedance. For example, if the total bio-impedance consist of a 10 mΩ undulation superimposed on a 1 mΩ static body impedance then a baseline of 1 mΩ static body impedance may be cancelled out using the second current while the 10 mΩ undulation is represented in the output voltage. If the reference current contained 0.1% noise the output voltage may contain noise corresponding to 0.01 mΩ. However, this may be dependent on the second current being derived from the same reference current as the first current such that part of the noise is cancelled. If the second current had been derived from e.g. a noise free source then the full noise of the 1 mΩ static body impedance, i.e. 1Ω, may be passed on to the transimpedance stage such that the output voltage would contain noise corresponding to 1Ω. This could effectively obscure the 10 mΩ undulation. Thus the invention may provide a high accuracy when measuring e.g. a small time variant bio-impedance even if it is superimposed on a large static bio-impedance.

The measurement unit according to embodiments of the invention may relieve the requirements on the dynamic range of the circuit reading out the output voltage. If the signal of interest is a small bio-impedance superimposed on a large bio-impedance the dynamic range may need to be large. If the small bio-impedance is separated from the large bio-impedance as provided by the measurement unit and the small bio-impedance is read out separately the dynamic range may be smaller.

The measurement unit according to embodiments of the invention may facilitate a 2-electrode setup. Even though a 2-electrode setup may add two electrode impedances to the measurement such that a small time variant bio-impedance is superimposed on the sum of the time invariant bio-impedance and the two electrode impedances, the measurement unit may make it possible to cancel also the two electrode impedances together with the time invariant bio-impedance. Thereby a 2-electrode setup may still provide sufficient accuracy while using conventional measurement unit may require a 4-electrode setup to reduce noise that depends on the electrode impedances.

The measurement unit according to embodiments of the invention may ensure that a biosignal measuring device may be small and thereby convenient to wear. This may be advantageous if the biosignal measuring device is to be fitted into e.g. a smartwatch. Using a 2-electrode setup may also reduce the size as compared to a 4-electrode setup. Furthermore, a measurement unit according to embodiments of the invention may relieve requirement of other noise cancelling apparatuses, thereby reducing the size.

The measurement unit according to embodiments of the invention may further ensure that the manufacturing cost for the biosignal measuring device is small. Reducing the number of electrodes, relieving requirement of other noise cancelling apparatuses, relieving the requirements on the dynamic range of the readout circuit, and relieving the requirements on a stable reference current source may facilitate providing an inexpensive product.

Further, the power consumption of a biosignal measuring device may be small thanks to using a measurement unit according to embodiments of the invention. In a conventional measurement unit, noise in the reference current may be mitigated with a high power consumption. However, this requirement may be alleviated using a measurement unit according to embodiments of the invention.

It should be understood that the measured bio-impedance according to embodiments of the invention may be the time variant part of the bio-impedance. It should also be understood that the measured bio-impedance may be the total bio-impedance. For example, in a 2-electrode setup the measurement unit may see the total bio-impedance plus the electrode impedances. The measurement unit may then cancel the part of the first current which represents the electrode impedances but keep the total bio-impedance. It should also be understood that the measured bio-impedance may be the time variant part of the bio-impedance plus part of the time invariant part of the bio-impedance.

It should be understood that the factor may be a constant or changed dynamically. For example, if it is known that a constant factor ensures that no more than 95% of the time invariant part of the bio-impedance is cancelled, while also ensuring that the absolute value of the difference between the first and the second current is below a threshold, that factor may always be used and still ensure an improvement in the accuracy of the measurement.

It should be understood that the threshold may be set such that the current that is passed from the transconductance stage to the transimpedance stage is not too large. The threshold may e.g. be based on the dynamic range of the circuit reading out the output voltage from the transconductance stage. The threshold may also be set based on an anticipated first current, e.g. based on an expectation of the bio-impedance to be measured and/or an expectation of the electrode impedances. The electrode impedance may e.g. depend on how good the conductance between the electrode and the skin of the body is.

The measurement unit may also be further configured to dynamically determine the factor by measuring the difference between the first and the second current.

An advantage may be that a good accuracy could be maintained over time. This may be ensured by accounting e.g. for changes in the measurement conditions. For example, if it is expected that a bio-impedance measurement targeting respiration will result in a sinusoidal variation of the first current with an amplitude of 1 mA and a frequency of 1 Hz, then the threshold may be set to e.g. 4 mA. A difference between the first and second current may e.g. be measured during a time interval longer than the inverse of the frequency, e.g. 5 times the inverse of the frequency. If the absolute value of the average of the difference is larger than 4 mA the factor is changed. If the first current is a 1 mA sinusoidal variation superimposed on a 103 mA constant current and the reference current is 2 mA then the factor may be set to 50. The difference between the first and second current that is passed on to the transimpedance stage may then be a 1 mA sinusoidal variation superimposed on a 3 mA constant current. However, as the subject of the measurement moves the electrode impedances may change which also changes the first current. Several measurements of the difference between the first and second current may be performed, e.g. periodically, e.g. every second or every minute. The factor may then be adjusted if necessary.

The threshold may also be based on an anticipated variation in bio-impedance. An advantage may be that the accuracy of a measurement of the varying bio-impedance is improved. The variation may be anticipated based on a theoretical prediction or based on a measured prediction. It may e.g. be predicted theoretically that due to heart beat modulation of the blood flow the bio-impedance should vary by a certain amount when the electrodes are placed in certain positions on the body, e.g. on the wrist with a given electrode separation. A measured prediction may also be based on past measurements of a bio-impedance. For example, one may start out with a large threshold and a small factor to perform a rough measurement after which the threshold may be reduced based on a first measurement result.

The anticipated variation in bio-impedance may be a variation caused by respiration or heart beats.

This implies that the measurement unit may be particularly suitable for use in bio-impedance measurements for detecting respiration or heart beats.

The baseline cancellation current circuit of the measurement unit may comprise a digital controller and a baseline cancellation current digital-to-analog converter (IDAC), wherein the digital controller is configured to measure the difference between the first and the second current; calculate the factor based on the difference between the first and the second current; and deliver a factor signal, the factor signal being a signal representation of the factor, wherein the baseline cancellation IDAC is configured to receive the factor signal and the reference current and output the second current as the reference current multiplied by the factor.

It should be understood that the factor signal may be a digital representation of a number, e.g. an integer value represented in binary code.

An advantage may be that the factor signal produced by the digital controller may also be used for other purposes than controlling the IDAC. For example, the factor signal may be used to extract impedance information regarding the measurement. Such information may be e.g. information regarding the time invariant impedance of the body, which may be useful when assessing the health or state of the body. When such impedance information is combined with impedance information derived from the output voltage the total bio-impedance may be reconstructed while still maintaining a good SNR for the time variant part of the bio-impedance. Impedance information regarding the measurement may also be e.g. information regarding the electrode impedance or information regarding how much the electrode impedance fluctuates etc. This may be used to improve the measurement. For example, information regarding the electrode impedance may be used to detect if the electrode connection is poor such that the user may be notified.

The measurement unit may further comprise a first and a second body tissue electrode which are configured to provide an electric connection to a body at a first and a second position respectively, wherein the measurement unit is further configured to drive the measurement current through the body tissue between the first and second positions.

An advantage of providing a measurement unit with a first and a second body tissue electrode may be that the electrode impedance may be anticipated. The electrode impedance may depend on e.g. the electrode size, the electrode surface structure, the electrode material etc. If the electrode type is known the electrode impedance may be anticipated which may affect e.g. how much the reference current should be amplified. If the electrodes are not included in the measurement unit, such that third party electrodes may be used, important information for the settings of the measurement unit may be lost.

The measurement unit may be further configured to acquire the measurement voltage as a voltage between the first and the second body tissue electrode.

This facilitates providing a bio-impedance measuring device that is small and thereby convenient to wear. Using the first and the second body tissue electrode both for driving the measurement current through the body tissue and for acquiring the measurement voltage, i.e. a 2-electrode setup, may reduce the size of the bio-impedance measuring device as compared to using a 4-electrode setup. Furthermore, just as using known electrodes for driving the measurement current through the body tissue has an advantage there is also an advantage in using known electrodes for acquiring the measurement voltage. If the electrode type is known the electrode impedance may be anticipated and this may e.g. affect the choice of the threshold.

The measurement unit may further comprise a third and a fourth body tissue electrode which are configured to provide an electric connection to the body at a third and a fourth position respectively, wherein the measurement unit is further configured to acquire the measurement voltage as a voltage between the third and the fourth positions.

An advantage may be that the accuracy may be improved further if separate electrode pairs are used for driving the measurement current and for acquiring the measurement voltage, i.e. a 4-electrode setup. Combining the advantages of removing the electrode impedance from the signal going into the transconductance stage, such that the measurement voltage only represents the total bio-impedance, with the advantage of selecting part of the total bio-impedance by cancelling a baseline may give a better accuracy than either of the methods could provide on their own.

The measurement unit may be further configured to extract a baseline impedance from the factor, the baseline impedance representing a time invariant impedance of the body.

It should be understood that the factor may be a measure of how much baseline current is subtracted from the first current before passing it on to the transimpedance stage. Thus, as the first current may be a representation of a total impedance the factor may also be used to extract a corresponding baseline impedance. An advantage of extracting the baseline impedance from the factor may be that it facilitates reconstructing the total impedance from the factor and the output voltage. Extracting a time invariant impedance of the body may facilitate extracting important information regarding the health or state of the body, e.g. body fat content or body water content.

It should herein be understood that the baseline impedance may represent the entire time invariant impedance part of the body or a portion of the time invariant impedance part of the body. It should also be understood that the baseline impedance may represent a time invariant impedance part of the body together with an additional impedance, e.g. an electrode impedance.

The measurement unit may be further configured to extract an impedance variation from the output voltage, the impedance variation representing a time variant impedance of the body.

An advantage may be that a time variant part of the bio-impedance may be extracted with high accuracy. This may facilitate dynamically measuring changes in the body.

The measurement unit may be further configured to output a respiration signal based on the impedance variation.

It should be understood that a respiration signal may relate to a varying bio-impedance signal caused by movements of the chest or lungs during respiration. Thus, a respiration signal may be based on the impedance variation. The respiration signal may further be used such that parameters such as respiration rate or lung volume changes during inhalation and/or exhalation may be extracted.

The measurement unit may be further configured to output a cardiac signal based on the impedance variation.

It should be understood that a cardiac signal may relate to a varying bio-impedance signal caused by movements of the heart. Thus, a cardiac signal may be based on the impedance variation. The cardiac signal may further be used such that an electrocardiograph signal may be extracted. Parameters such as e.g. heart rate, heart stroke volume, cardiac output, ventricular ejection time, pre-ejection period may also be extracted.

The measurement unit may comprise:

a first current modulator which is configured to modulate the first current at a first frequency; and a second current modulator which is configured to modulate the second current at the same first frequency, such that the modulation of the first current and the second current becomes synchronized.

Such a measurement unit may facilitate measurements wherein the measurement current is modulated such that the bio-impedance may be measured at a non-zero frequency. It should herein be understood that the first current modulator may be a combination of a measurement current modulator and a demodulator. The measurement current modulator may modulate the measurement current at a measurement frequency such that the measurement voltage also becomes modulated at the same measurement frequency. The demodulator may then demodulate the signal from the measurement voltage such that the first current becomes modulated at the first frequency, wherein the first frequency is different from the measurement frequency. However, it should also be understood that the first current modulator may be a modulator which directly modulates the measurement current at the first frequency such that the first current also becomes modulated at the first frequency. In some embodiments the first frequency may thus be the same as the measurement frequency. The second current modulator may then modulate the second current also at the first frequency such that the measurement unit modulates the first and the second current at the same frequency.

Modulation of the measurement current may mean that the body tissue electrodes do not need to be in conductive contact with the body. It may be sufficient with a capacitive contact. It may then be possible to use electrodes on top of a person's clothing, e.g. electrodes in a car seat such that a driver may be monitored while driving. Modulation of the first and second current using the same frequency may ensure that noise originating from the reference current will be reduced during bio-impedance measurements at a non-zero frequency.

The IA of the measurement unit may be configured to have a gain above 100 V/V.

An advantage may be that the IA may introduce less noise when operating at higher gain. In a conventional measurement unit the measurement voltage may itself be large and it may not be possible to use a high gain without generating a very large output voltage. In contrast, when using a measurement unit according to embodiments of the invention, most of the signal representing the bio-impedance may be removed through baseline cancellation such that it is only a small portion, representing e.g. the time variant part of the bio-impedance that is actually amplified in the output voltage. Thus, a high gain may be used which further improves the accuracy of the measurement unit.

According to another embodiment of the invention, there is provided a biosignal measuring device comprising a measurement unit according to embodiments of the invention. The biosignal measuring device may be implemented, for example, in a wristwatch or a health patch. The measurement unit according to embodiments of the invention may be implemented in an integrated circuit comprising additional elements or units of the biosignal measuring device.

The term 'wristwatch' may herein refer to a timepiece designed to be worn around the wrist of a person. The wristwatch may be a smartwatch wherein the smartwatch is a wearable processing device that may process a signal from the measurement unit. The wristwatch may also be configured to pass on a signal from the measurement unit to a processing device, e.g. pass on the signal wirelessly. Thus the wristwatch may not necessarily need to be a processing device itself. The wristwatch may comprise electrodes for the measurement unit which are in contact with a person's skin while the person is wearing the wristwatch. The wristwatch may e.g. monitor, among other biosignals, a cardiac signal from the person.

The term 'health patch' may herein refer to a patch which may be attached to the body of a person, e.g. adhesively attached. The health patch may e.g. be adhesively attached to the chest of a person. The health patch may comprise electrodes for the measurement unit which are in contact with a person's skin while the person is wearing the health patch.

The health patch may comprise a processing device that may process a signal from the measurement unit or pass on a signal from the measurement unit to a processing device, e.g. pass on the signal wirelessly. Thus the health patch may not necessarily need to comprise a processing device itself. The health patch may e.g. monitor, among other biosignals, a cardiac signal or a respiration signal from the person.

Effects and features of this embodiment are generally analogous to those described above in connection with the measurement unit.

A particular advantage of a biosignal measuring device according to the invention may be that a bio-impedance signal from a person may be monitored over an extended period of time. Further, the measurement unit may, as discussed above, be small which implies that smartwatches or health patches including the measurement unit may also be small and thereby convenient to wear. This may be particularly important when the bio-impedance signal should be monitored over an extended period of time.

BRIEF DESCRIPTION OF THE DRAWINGS

The above, as well as additional objects, features and advantages of the present inventive concept, will be better

DETAILED DESCRIPTION

In cooperation with attached drawings, the technical contents and detailed description of the present invention are described hereinafter according to a preferable embodiment, being not used to limit the claimed scope. This invention may be embodied in many different forms and should not be construed as limited to the embodiments set forth herein; rather, these embodiments are provided for thoroughness and completeness, and fully convey the scope of the invention to the skilled person.

Figure 1:
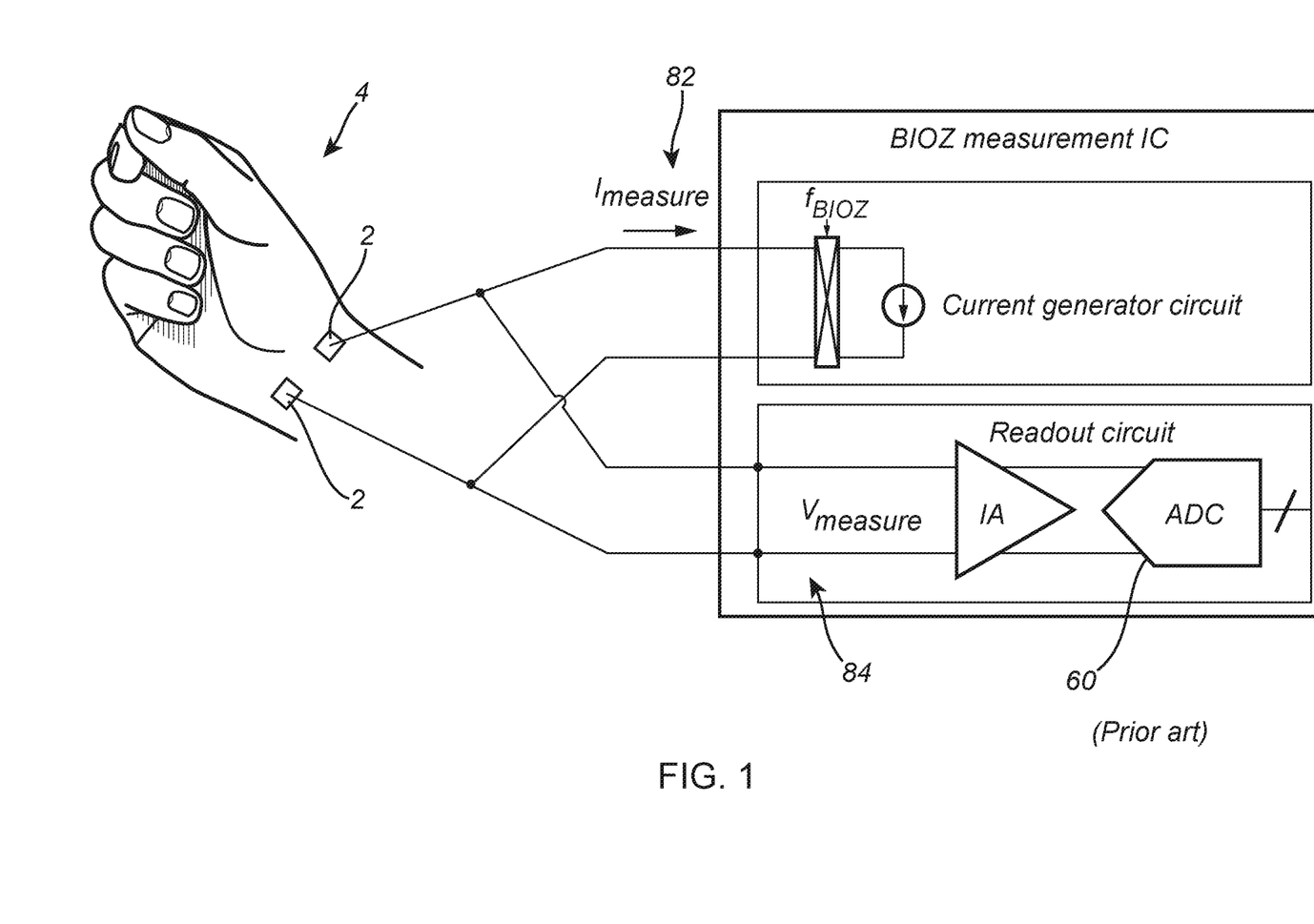
FIG. 1 illustrates a prior art measurement setup for bio-impedance measurements.
Figure 2:
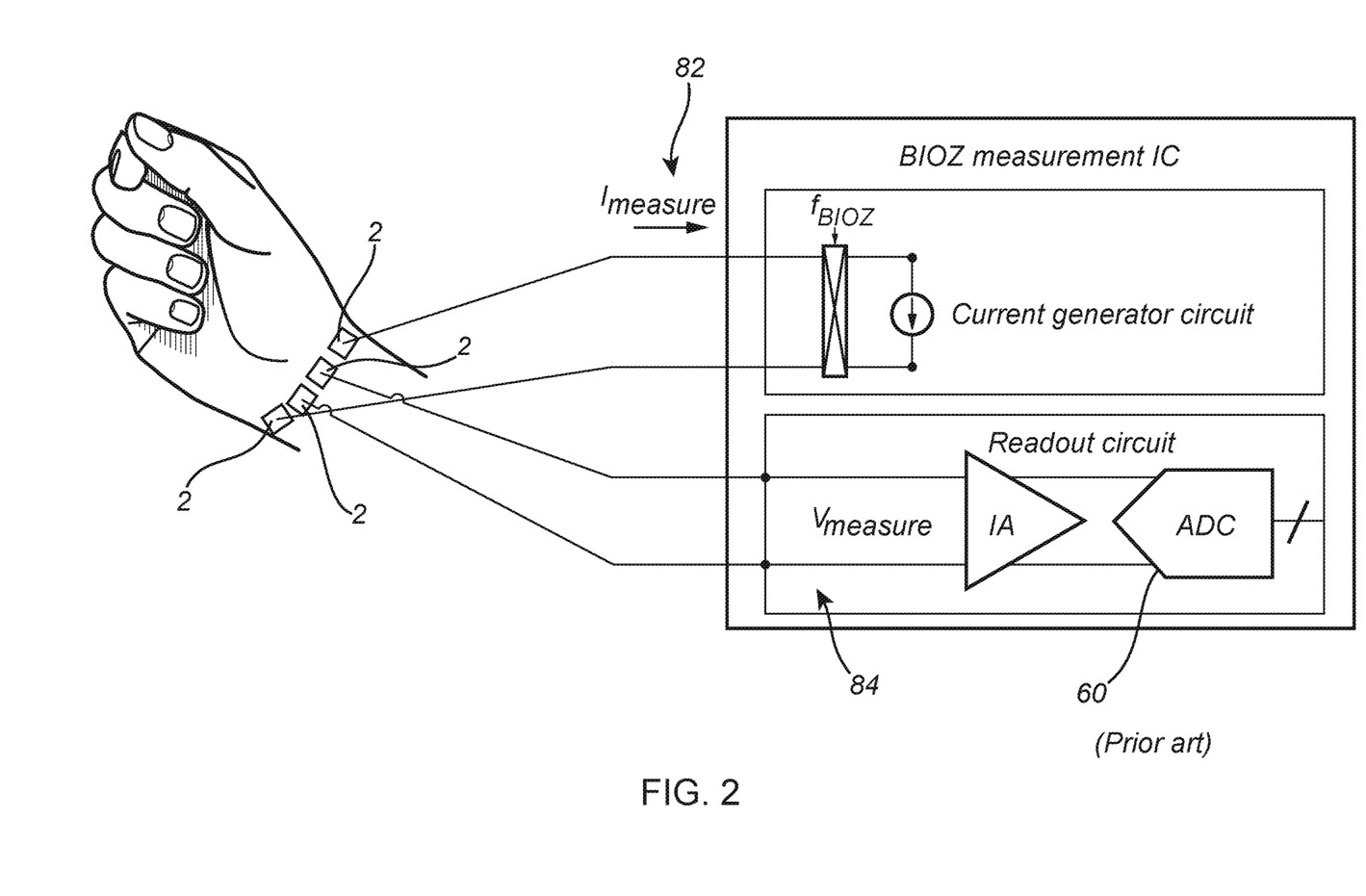
FIG. 2 illustrates a prior art measurement setup for bio-impedance measurements.

FIGS. 1 and 2 illustrate conventional prior art measurement setups for bio-impedance measurements. In prior art bio-impedance measurements a current generator produces a measurement current 82. The measurement current 82 flows between two electrodes 2 through part of a body 4, e.g. a wrist. Due to the bio-impedance of the body 4 a measurement voltage 84 is produced. The measurement voltage 84 may then be recorded by a readout circuit wherein an instrumentation amplifier amplifies the signal which is subsequently converted to a digital signal through an analog to digital converter 60. FIG. 1 illustrates a measurement setup wherein the same electrode pair is used for driving the measurement current 82 through the body as for measuring the measurement voltage 84, i.e. a 2-electrode setup. FIG. 2 illustrates a measurement setup wherein one pair of electrodes is used to drive the measurement current 82 and a second pair of electrodes is used to measure the measurement voltage 84, i.e. a 4-electrode setup. A 4-electrode setup is often used to improve the accuracy. However, a 4-electrode setup may be less convenient for the subject of the bio-impedance measurement.

Figure 3:
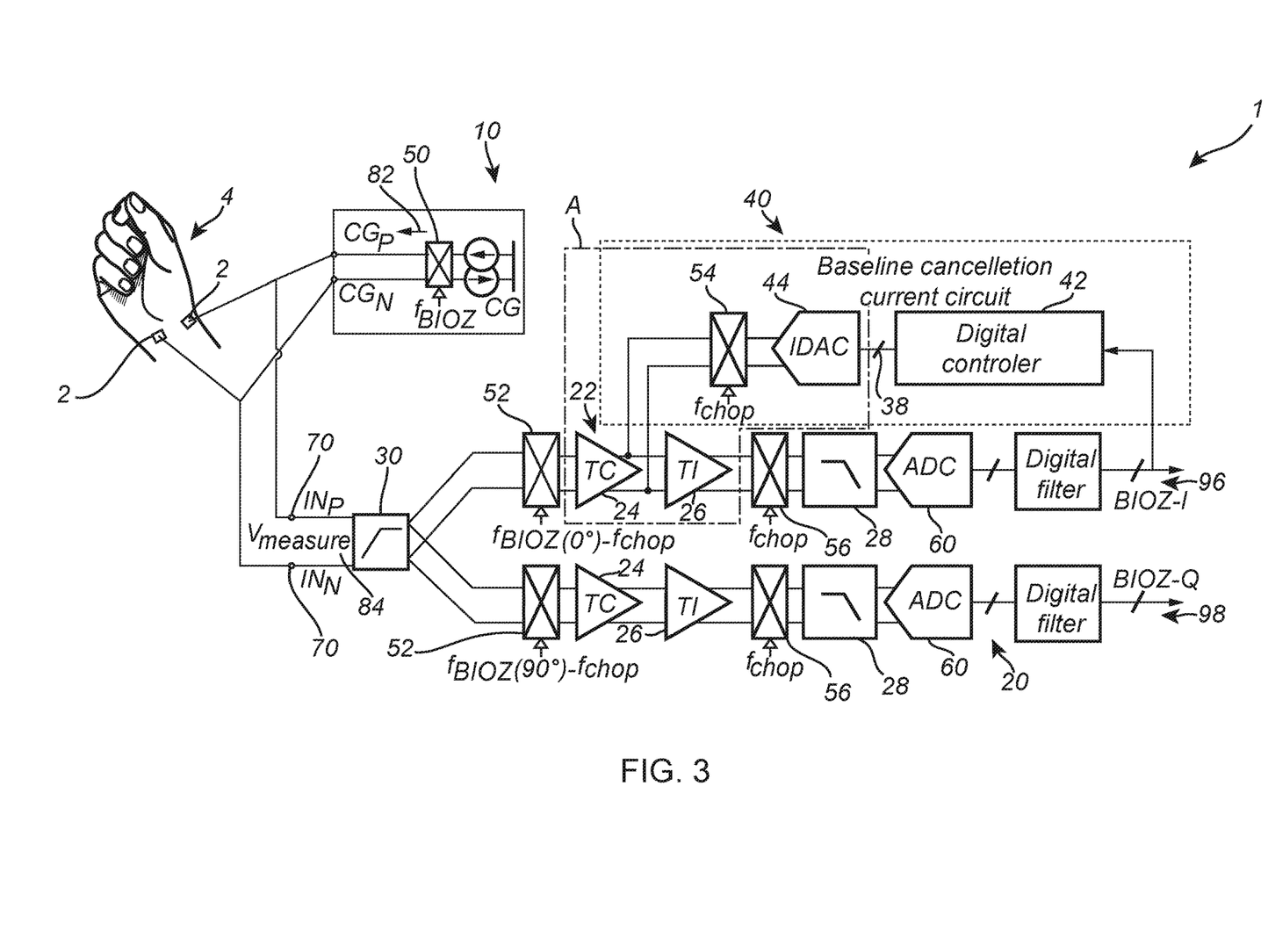
FIG. 3 illustrates a measurement unit and a measurement setup for bio-impedance measurements on a wrist.

FIG. 3 illustrates a measurement unit 1 and a measurement setup for bio-impedance measurements on a wrist according to an example embodiment of the invention. The measurement setup illustrated uses a 2-electrode setup. However, the measurement setup may also be used with a 4-electrode setup or a setup with any number of electrodes 2 larger than one.

The electrodes 2 may be conductive or capacitive to provide an electric connection to a body. An example of conductive electrodes 2 may be conductive plates, e.g. aluminum plates, covered with hydrogel. Herein the hydrogel may act as an adhesive as well as an electrolytic medium between the conductive plate and the skin. An example of capacitive electrodes 2 may be a conductive plate in contact with the skin without any intermediate hydrogel or a conductive plate with an insulating layer in-between the plate and the skin. A current may be driven through a part of a body 4 by allowing the current to flow through one electrode 2 via the part of the body 4 into the other electrode 2. Alternatively, a current may be driven through a part of a body 4 by supplying an alternating voltage between two electrodes such that a current is capacitively induced in the body 4.

In the embodiment of FIG. 3 alternating currents are used to measure a bio-impedance at a non-zero frequency. FIG. 3 thus includes a number of modulators which are used to generate alternating currents. It should be understood that the currents in the transconductance 24 and transimpedance stage 26 of a measurement unit 1 for measuring a bio-impedance at non-zero frequency may correspond to the currents in the transconductance 24 and transimpedance stage 26 of a measurement unit 1 for measuring a bio-impedance at zero frequency, albeit at a different frequency.

In the setup illustrated in FIG. 3 the measurement unit 1 comprises a current generator circuit 10, a readout circuit 20 and a baseline cancellation current circuit 40. In the illustrated measurement unit 1 the current generator circuit 10 produces a measurement current 82. The measurement current 82 flows between two electrodes 2 through a part of a body 4. Due to the bio-impedance of the body 4 a measurement voltage 84 is produced. In the illustrated measurement setup the readout circuit 20 is connected to the same two electrodes 2 as the current generator circuit 10. The measurement voltage 84 between the two electrodes 2 may be taken as input for the readout circuit 20.

The current generator circuit 10 of the measurement unit 1 may comprise a device for amplifying a reference current 80 (the reference current will be discussed in more detail in connection to FIG. 7). The device for amplifying a reference current 80 may be a current amplifier, it may also be a current mirror with a transfer ratio of one or more, it may also be multiple current mirrors with transfer ratios of one or more wherein the multiple current mirrors are connected to collectively supply an amplified current. The device for amplifying a reference current 80 may also be a variable current mirror with an adaptive length shift register for flexible current amplification. The current generator circuit 10 may further comprise a measurement current modulator 50 which modulates the amplified current to form a modulated measurement current 82, e.g. a square wave with a modulation frequency of $F_{BIOZ}$. The modulation frequency may be e.g. a frequency in the range of 1 KHz to 1 MHz.

The readout circuit 20 of the measurement unit 1 in FIG. 3 has two input nodes 70 between which the measurement voltage 84 arises. The readout circuit 20 may further comprise a high pass filter 30 which may suppress frequencies in the measurement voltage 84 below $F_{BIOZ}$, as illustrated in the figure. DC electrode offset may thus be suppressed.

The measurement unit 1 in FIG. 3 is configured to measure a resistance part of the bio-impedance and a reactance part of the bio-impedance. The readout circuit 20 herein comprise a first branch 96 which reads out the resistance part of the bio-impedance and a second branch 98 which reads out the reactance part of the bio-impedance, as illustrated in the figure.

Figure 4:
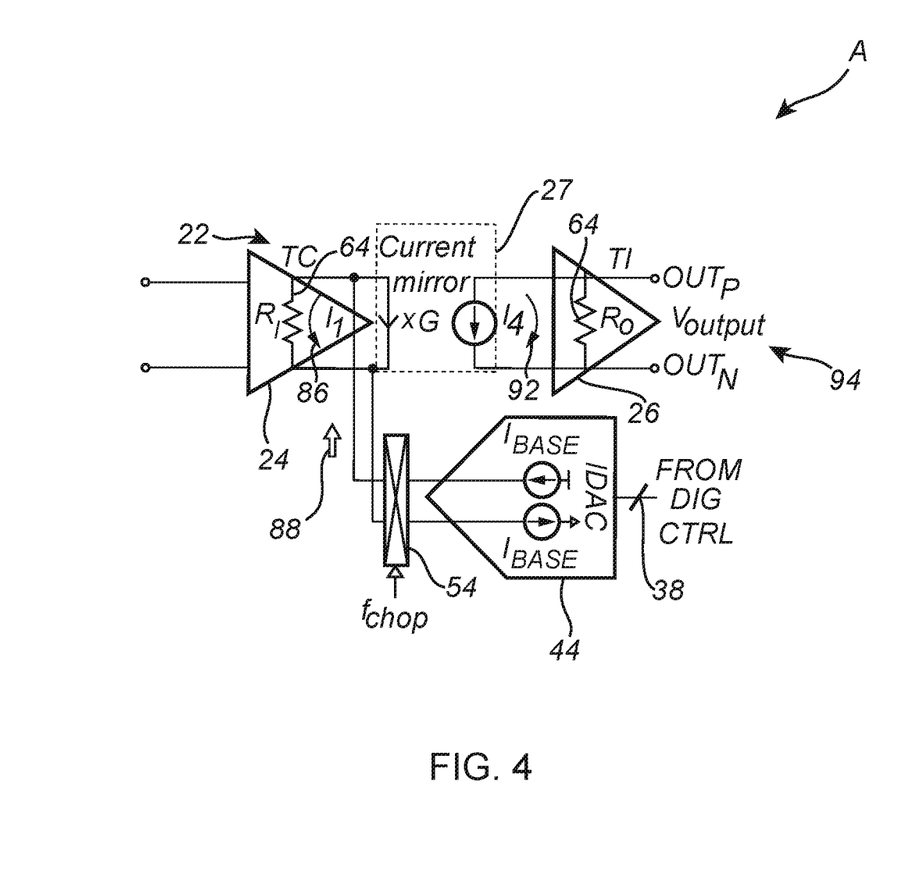
FIG. 4 illustrates a part of a measurement unit.

In the following the first branch 96 is described, the details of how the TC 24 and TI 26 stage may be implemented are illustrated in the more detailed views of FIG. 4 and FIG. 6. The first branch 96 may comprise a demodulator 52 which demodulates the signal from $F_{BIOZ}$ to a chopping frequency $f_{chop}$. $f_{chop}$ may be lower than $F_{BIOZ}$, $f_{chop}$ may be e.g. 8 kHz. By demodulating to a lower frequency the measurement unit 1 may consume less power than if no demodulation was used. By demodulating to a lower frequency the requirements on the components of the read out circuit may also be lowered. Components designed for lower frequencies may be cheaper than components designed for higher frequencies. The demodulator 52 in the first branch 96 may demodulate from $F_{BIOZ}$ to $f_{chop}$, wherein the demodulation may be done in phase, i.e. 0° phase difference, with the modulation of the measurement current 82. Thus the signal from the first branch 96 may be used to retrieve the resistance part of the bio-impedance as a resistance may cause a voltage drop in phase with the current. The first branch 96 may further comprise an instrumentation amplifier (IA) 22, which in turn comprises a TC stage 24 and a TI stage 26, and a baseline cancellation current circuit 40.

The part marked A in the circuit in FIG. 3 will now be described in more detail. One implementation of part A is illustrated in FIG. 4. It should however be understood that there may be other ways to implement part A. The following discussion should be read with reference to both FIG. 3 and FIG. 4. The measurement voltage 84, or a demodulated version of the measurement voltage, may be converted to a first current ($I_1$) 86 in the transconductance stage 24 wherein the first current 86 is proportional to the measurement voltage 84. This may e.g. be done by applying the measurement voltage 84 across a resistor 64 such that the first current 86 runs through the resistor 64. The measurement voltage 84 may be seen as a representation of the total bio-impedance and as the first current 86 is proportional to the measurement voltage 84 the first current 86 may also be seen as a representation of the total bio-impedance. The IA 22 may further comprise a current mirror 27 which mirrors a current from the TC stage 24 to the TI stage 26 to produce an output voltage 94 which may be proportional to the passed on current. The IA 22 does not merely pass on the first current 86 from the TC stage 24 to the TI stage 26. Rather, the TC stage 24 receives a second current ($I_2$) 88 from the baseline cancellation current circuit 40. The baseline cancellation current circuit 40 may comprise a digital controller 42 and a baseline cancellation current digital-to-analog converter (IDAC) 44. The baseline cancellation current circuit 40 may be configured to amplify the reference current 80 by a factor 36 (the factor 36 will be described in more detail in connection with FIG. 7) to form the second current 88. In order to match the current modulation of the first current 86 the baseline cancellation current circuit 40 may further comprise a cancellation current modulator 54 which operates at the frequency $f_{chop}$, such that the second current 88 is modulated at this frequency. The TC stage 24 may thus receive the second current 88 from the baseline cancellation current circuit 40 such that a third current 90 is formed, the third current 90 being the difference between the first 86 and the second 88 current. The third current 90 may subsequently be passed on to the TI stage 26, e.g. by current mirroring, to form a fourth current 92. Thus, the IA 22 may mirror the difference between the first current 86 and the second current 88. The IA 22 may e.g. mirror the difference between the first current 86 and the second current 88 to the fourth current ($I_4$) 92:

$$I_4 = I_1 - I_2,$$

or introduce a gain such that the current passed on is an amplified version of the difference between the first current 86 and the second current 88:

$$I_4 = G^*(I_1 - I_2),$$

wherein G represents the gain. The fourth current may thus be e.g. $I_4 = I_3$ or $I_4 = G^*I_3$. The TC stage 24 may then produce the output voltage 94 such that the output voltage 94 is proportional to a difference between the first current 86 and the second current 88. This may e.g. be done by passing the fourth current 92 through a resistor 64 such that the output voltage 94 is formed across the resistor 64.

The signal represented by the output voltage 94 may subsequently be passed through a baseband demodulator 56 which operates at the frequency $f_{chop}$ and a low pass filter 28. The baseband demodulator 56 may demodulate the signal to its baseband form; wherein, nominally, the only modulation in the signal is the modulation which originates from time-dependent changes in the bio-impedance. Thus the demodulator 52, the baseband demodulator 56 and the low pass filter 28 together sets a measuring bandwidth of analog front-end. The measuring bandwidth may be e.g. 3 kHz. The signal may subsequently be passed through an analog to digital converter 60 and possibly digitally filtered. A digital signal may thus be acquired which together with a signal describing the measurement current 82 may be used to retrieve the resistive part of a measured bio-impedance, wherein the measured bio-impedance may be e.g. the time variant part of the total bio-impedance, as defined by the difference between the first 86 and the second 88 current. The resistive part of a measured bio-impedance may e.g. be acquired by dividing the digital signal from the first branch 96 with the signal describing the measurement current. It should be understood that there may be other ways to convert the signal to a baseband form without using a baseband demodulator 56 and a low pass filter 28. For example, the output voltage may be passed to the analog to digital converter 60 directly, after which the baseband signal may be extracted may be extracted digitally.

The digital signal outputted by the first branch 96 may also be used as feedback to the baseline cancellation current circuit 40. The digital signal outputted by the first branch 96 may herein be seen as a representation of the difference between the first 86 and second 88 current, $I_1 - I_2$. The digital controller 42 may thus be configured to use the digital signal outputted by the first branch 96 to set the factor 36 such that that the absolute value of the difference between the first 86 and the second 88 current is below a threshold 34 during the measurement of the bio-impedance. This may e.g. be done by repeatedly checking the average of the digital signal outputted by the first branch 96 during a time period, e.g. 0.5 s, and changing the factor 36 if the absolute value of the time period average for $I_1 - I_2$ is above the threshold 34 and keeping the factor 36 if the absolute value of the time period average for $I_1 - I_2$ is below the threshold 34. An example of an algorithm for adjusting the factor 36 to keep $I_1 - I_2$ within ±150 nA, i.e. using a threshold 34 of 150 nA, when the reference current is 250 nA may be:

```
if (-150nA< I_1 - I_2 <150nA)
    I_2 = I_2
else if (I_1 - I_2 >150nA)
    factor=factor+round((I_1 - I_2)/250nA)
    I_2 = factor*250nA
else if (I_1 - I_2 <-150nA)
    factor=factor-round((I_2-I_1)/250nA)
    I_2 = factor*250nA
```

Herein the operation round refers to rounding to an integer value.

The digital controller 42 may then output a factor signal 38 which is passed on to the IDAC 44. The factor signal 38 may e.g. be a digital signal representing the factor 36. The factor signal 38 may e.g. be a digital signal representing an integer wherein the integer is the factor 36. The IDAC 44 may subsequently multiply the factor signal with the reference current 80, the reference current 80 for the IDAC 44 being the same as the reference current 80 used by the current generator circuit 10. Thus the reference current 80 may be amplified by the factor 36 to form the second current 80 which is then delivered to the TC stage 24. The amplification may be implemented e.g. by the factor signal 38 being used by the IDAC 44 to activate a number of current mirrors, wherein the number of current mirrors determines the amplification.

In the following the second branch 98 is described. The second branch 98 may be similar to the first branch 96. However, the second branch 98 may lack a baseline cancellation current circuit 40 as noise originating from the reference current 80 may not be as severe in the second branch 98 as in the first branch 96. In FIG. 3 there is no baseline cancellation current circuit 40 in the second branch 98. However, the second branch 98 may also comprise a baseline cancellation current circuit 40 configured analogously to the baseline cancellation current circuit 40 in the first branch 96. The reactance part of a measured bio-impedance may e.g. be acquired by dividing the digital signal from the second branch 98 with the signal describing the measurement current. The second branch 98 may comprise a demodulator 52 which may demodulate the signal from $F_{BIOZ}$ to a chopping frequency $f_{chop}$. The demodulator 52 in the second branch 98 may demodulate from $F_{BIOZ}$ to $f_{chop}$, wherein the demodulation may be done at a 90° phase difference compared to the modulation of the measurement current 82. Thus the signal from the second branch 98 may be used to retrieve the reactance part of the bio-impedance as a reactance may cause a voltage drop 90° out of phase with the current.

In the above description of FIG. 3 the measurement current 82 is modulated at a frequency $F_{BIOZ}$ using the measurement current modulator 50 and the readout circuit 20 comprises a demodulator 52 which demodulates the signal from $F_{BIOZ}$ to a chopping frequency $f_{chop}$. Thus the demodulator 52 acts as a first current modulator which is configured to modulate the first current at a frequency, the frequency being $f_{chop}$. In the above description the cancellation current modulator 54 then modulates the second current at the frequency $f_{chop}$. Thus the cancellation current modulator 54 may be seen as a second current modulator which is configured to modulate the second current at the same frequency as the first current modulator, such that the modulation of the first current and the second current becomes synchronized. However, it should be understood that in other embodiments there may be no demodulation in the readout circuit 20. In this case the measurement current modulator 50 may act as the first current modulator, modulating the current at the frequency $F_{BIOZ}$. The cancellation current modulator 54 may then act as a second current modulator which is configured to modulate the second current at the same frequency as the first current modulator. Thus in this case the cancellation current modulator 54 may also operate at the frequency $F_{BIOZ}$. It should also be understood that in some embodiments the high pass filter 30 and the low pass filter 28 may not necessarily be used. It should also be understood that in some embodiments, a bio-impedance at zero frequency may be of interest, in such an embodiment modulators and demodulators may not necessarily be used. It should also be understood that in some embodiments the baseline cancellation circuit 40 may be connected to either of the first 96 or the second 98 branch of the readout circuit 20. There may also be embodiments where there is one baseline cancellation circuit 40 connected to the first branch 96 and another baseline cancellation circuit 40 connected to the second branch 98. It should also be understood that in some embodiments only the resistance part of the bio-impedance or only the reactance part of the bio-impedance may be of interest. In such embodiments it may be sufficient to include only one of the first 96 or second 98 branches of the readout circuit 20.

Figure 5:
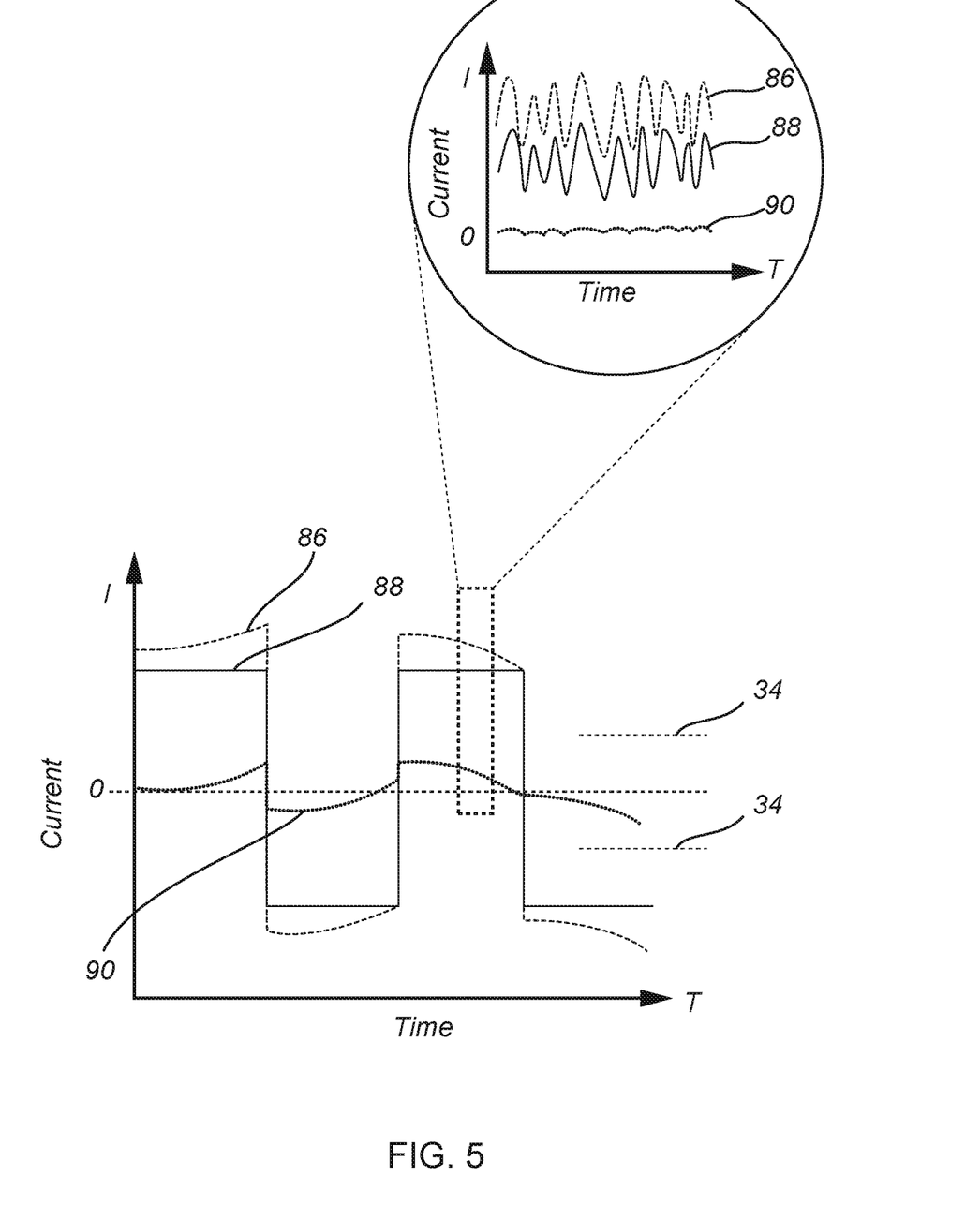
FIG. 5 illustrates how currents in a measurement unit may vary with time.

FIG. 5 exemplifies how the first 86, second 88 and third 90 current may vary with time. In this example, measurement current 82 is modulated by a square wave. Had the bio-impedance been completely time invariant, the first current 86 would also be a square wave. However, if the bio-impedance has a time variant part superimposed on a static part, then this time variation may also be evident in the first current 86 as seen in FIG. 5. A baseline may be subtracted from the first current 86 by the introduction of the second current 88 in the TC stage 24, FIG. 5 exemplifies a second current 88 constructed to recreate what the first current 86 would look like if it had only represented the time invariant part of the bio-impedance. FIG. 5 further illustrates how the third current 90 may vary with time, the third current 90 being $I_3=I_2-I_2$. The third current 90 may subsequently be passed on to the TI stage 26, e.g. by current mirroring, to form the fourth current 92. The fourth current may then be e.g. $I_4=I_3$ or $I_4=G*I_3$.

The close-up view of FIG. 5 illustrates an example of how the noise of the first 86, second 88 and third 90 current may vary with time.

According to embodiments, both the measurement current 82 and the second current 88 are derived from the same reference current 80. As the first current 86 may be derived from the measurement current 82 which in turn may be derived from the reference current 80 the first current 86 may have the same or similar noise characteristics as the reference current 80. As the second current 88 may be derived from the reference current 80 the second current 88 may have the same or similar noise characteristics as the reference current 80. Thus, the noise in the first current 86 may be correlated with the noise in the second current 88, as illustrated in the close-up view of FIG. 5. Thus, when subtracting the second current 88 from the first current 86, some of the noise may also be subtracted. Therefore, the noise of the third current 90 may be smaller than the noise of the first current 86, as seen in the close-up view of FIG. 5. Had the noise of the second current 88 been uncorrelated with the noise of the first current 86 the noise amplitude of the third current 90 may have been similar to the noise amplitude of the first current 86. This may have resulted in a substantially worse SNR for the third current 86 than for the first current 86, as a smaller signal with maintained noise amplitude may reduce the SNR. In contrast, according to embodiments, the SNR for the third current 86 may be similar to the SNR for the first current 86. The third current 90 may subsequently be converted to the fourth current 92 in the TI stage 26 and then to the output voltage 94 which may be digitalized to a signal representing the measured part of the total bio-impedance, in the above example the time variant part of the bio-impedance. The measurement unit may thus facilitate measuring part of a bio-impedance signal, e.g. the time variant part, with a SNR similar to the SNR of the total bio-impedance signal.

According to embodiments, the size of the part of the of the total bio-impedance signal that should be measured may be selected by the baseline cancellation current circuit 40 amplifying the reference current 80 by ensuring that the absolute value of the difference between the first 86 and the second 88 current is below a threshold 34 during the measurement of the bio-impedance. This may be done e.g. by a digital controller 42 dynamically determining the factor 36 by measuring the difference between the first 86 and the second 88 current. For example, by measuring the difference between the first 86 and the second 88 current every 0.5 second and adjusting the factor to keep the difference below the threshold 34. The threshold 34 may be based on an anticipated variation in bio-impedance. The variation may e.g. be anticipated based on a theoretical prediction or based on a measured prediction.

Once a bio-impedance measurement is performed wherein the factor 36 is kept constant during the measurement, the factor 36 itself may be used to extract a baseline impedance. The factor may represent the baseline current which is subtracted in the TC stage 24. When the baseline current is known the part of the measurement voltage 84 that it represents may be calculated which together with the measurement current 82 can be used to derive the baseline impedance. The output voltage 94, or a signal derived from the output voltage e.g. a signal from an analog to digital converter 60 may subsequently be used together with the measurement current 82 to derive the remaining impedance. Thus the total impedance may be reconstructed. For example, the time invariant bio-impedance may be derived from the factor 36 while the time variant impedance is derived from the output voltage.

Figure 6:
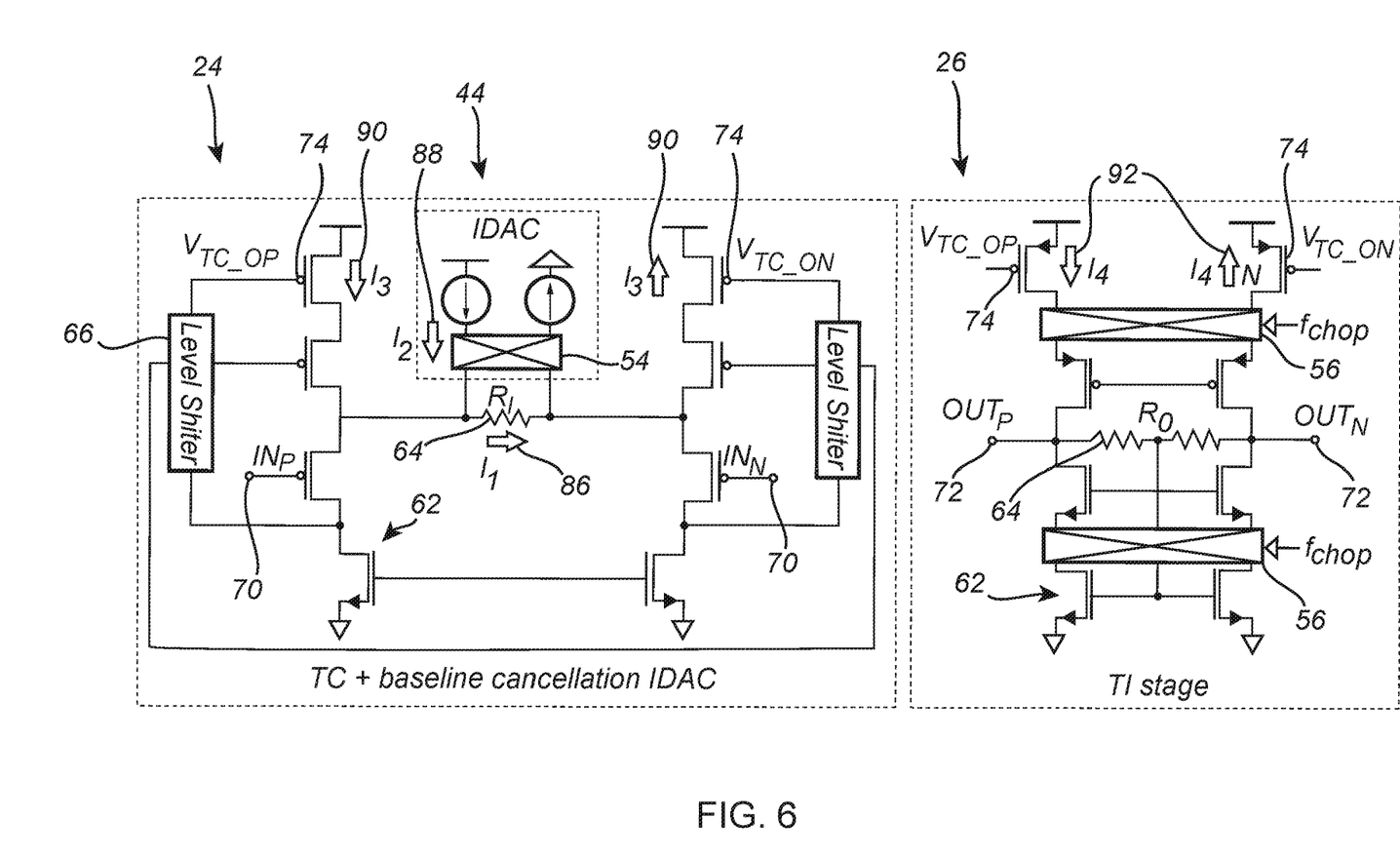
FIG. 6 illustrates a circuit diagram of a transconductance stage, a transimpedance stage and a IDAC in a measurement unit.

FIG. 6 illustrates a circuit diagram of how a TC stage 24, a TI stage 26 and a IDAC 44 may be implemented. The circuit comprises a number of transistors 62 and resistors 64 connected such that a measurement voltage 84 applied between input nodes 70 of the TC stage 24 may generate an output voltage 94 between output nodes 72. The measurement voltage 84 may appear across the resistor of the TC stage 24 to generate the first current 86, the first current may herein be the measurement voltage 84 divided by the resistance. By connecting the IDAC 44 across the same resistor 64 and driving the second current 88 through the resistor 64 of the TC stage 24 the third current 90 may be set to the difference between the first 86 and the second 88 current. The third current 90 in turn generates a voltage between the current mirror nodes 74. That voltage is subsequently passed on to the TI stage 26 and generates the fourth current 92 which in turn produces the output voltage 94 between output nodes 72 due to the resistors 64 of the TI stage 26. The circuit diagram also illustrates a cancellation current modulator 54 associated with the IDAC 44 and modulators 56 associated with the TI stage 26. Such modulators may facilitate measurements of an alternating measurement voltage 84. Additionally, the circuit diagram illustrates level shifter 66 which ensures the current mirror nodes 74 operates in the correct operating region, so that the third current 90 is mirrored to the fourth current 92. In some embodiments the shift register may be set such that the instrumentation amplifier 22 has a gain above 100 V/V, e.g. such that 1 mV between the input nodes 70 result in more than 100 mV between the output nodes 72.

Figure 7:
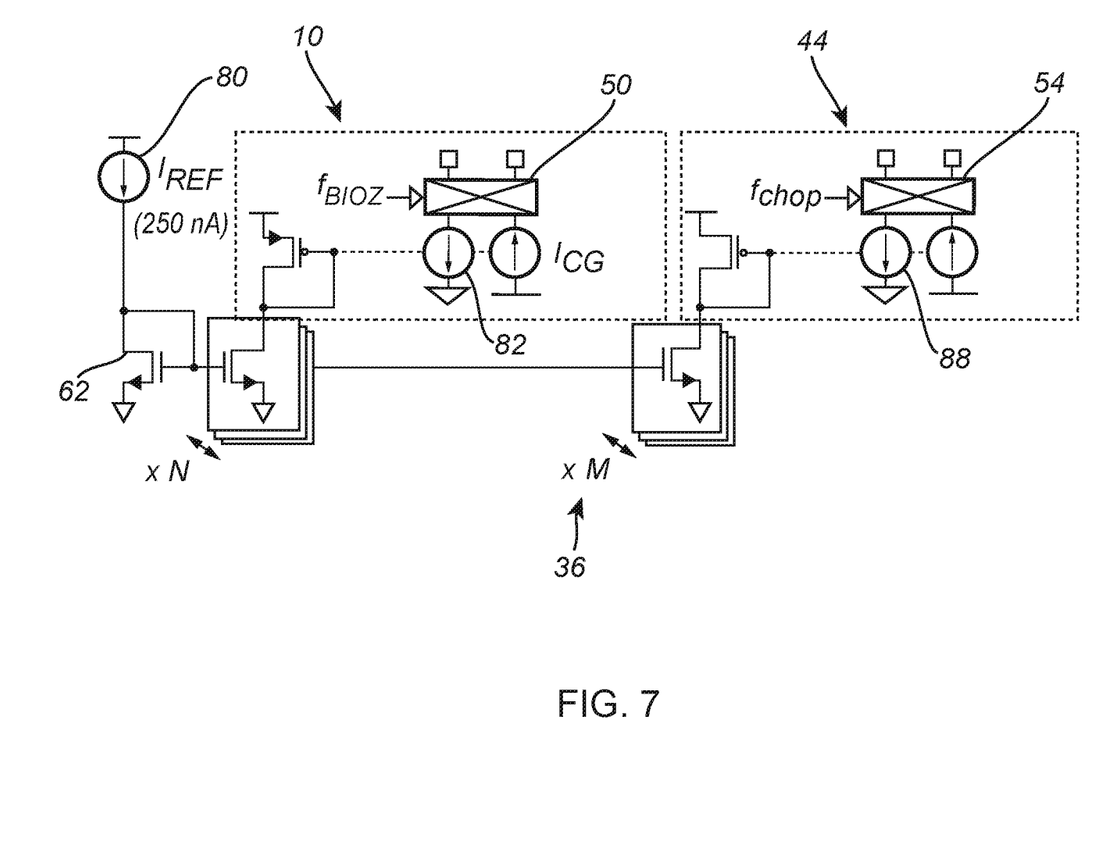
FIG. 7 illustrates a circuit diagram of a current generator circuit and an IDAC in a measurement unit.

FIG. 7 illustrates a circuit diagram of how a current generator circuit 10 and an IDAC 44 may be implemented to use the same reference current 80 to generate the measurement current 82 and the second current 88. The circuit comprises a number of transistors 62 connected to form a number of current mirrors. The illustrated circuit may mirror the reference current 80 to the current generator circuit 10 which in turn may amplify it using a variable current mirror with an adaptive length shift register wherein N transistors may be activated to amplify the reference current 80 N times. The illustrated circuit may further mirror the reference current 80 to the IDAC 44 which in turn may amplify it using a variable current mirror with an adaptive length shift register wherein M transistors may be activated to amplify the reference current 80 M times. The factor 36 may herein be M. Variable current mirrors of 1:N, for the current generator circuit 10, and 1:M, for the IDAC 44, may have dedicated an adaptive length shift register for flexible current amplification.

Figure 8:
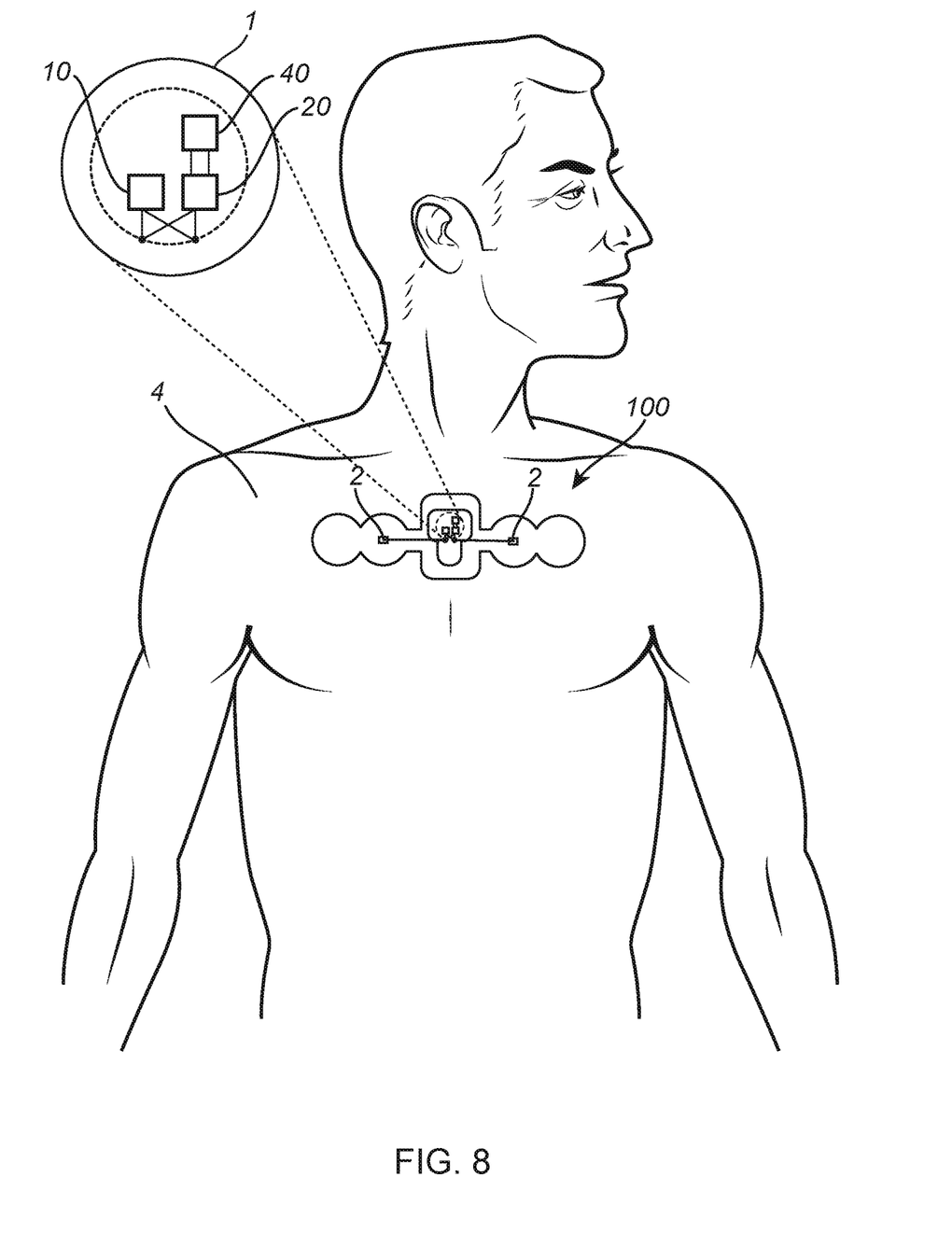
FIG. 8 illustrates a health patch comprising a measurement unit.
Figure 9:
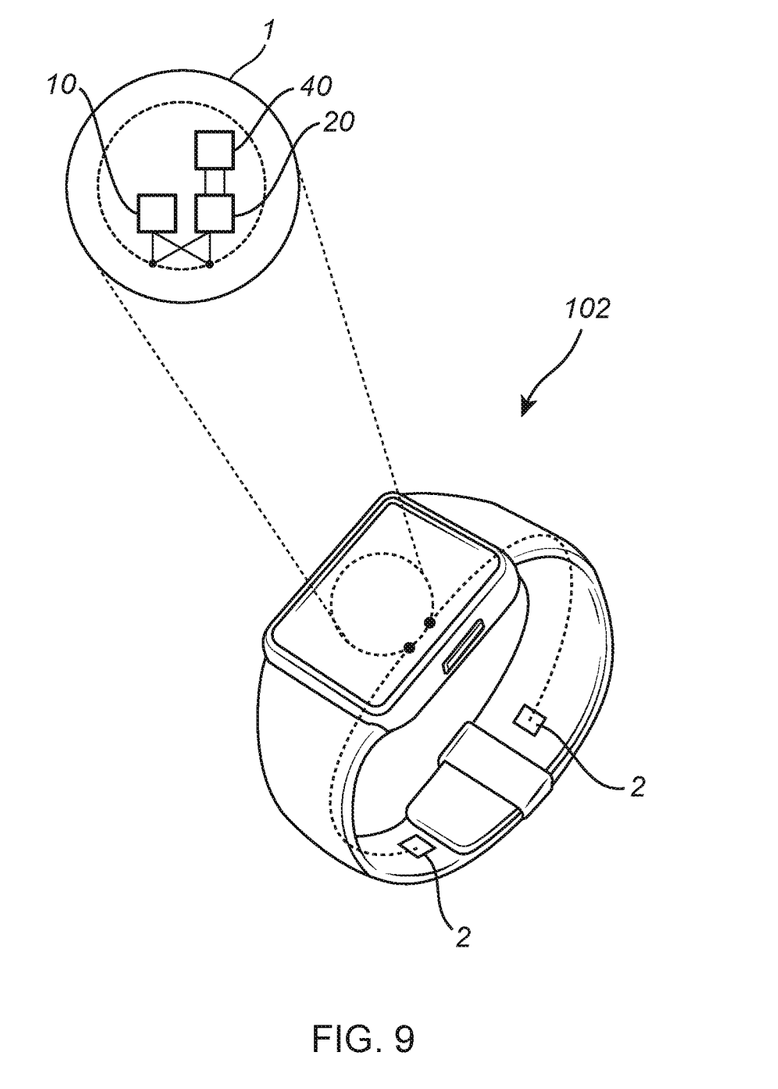
FIG. 9 illustrates a wrist watch comprising a measurement unit.

FIGS. 8 and 9 illustrate bio-impedance measuring devices, each comprising a measurement unit 1 according to example embodiments. In each of the illustrations, the measurement unit 1 comprises a current generator circuit 10, a readout circuit 20 and a baseline cancellation current circuit 40. In each of the illustrations, the measurement unit 1 is connected to two electrodes 2 which may be attached to a body 4. In FIG. 8 the measurement unit 1 is implemented in a health patch 100 and in FIG. 9 the measurement unit 1 is implemented in a wristwatch 102.

The health patch 100 may be a disposable patch attached to a reusable circuitry comprising the measurement unit 1. The patch may be adhesively attached to a body 4, in FIG. 8 it is attached to the chest of a person. The health patch 100 may e.g. be configured to capture changes in lung volume by placing the electrodes 2 such that the bio-impedance between the two electrodes changes with the movements of the lungs. The measurement unit 1 may be configured to output a respiration signal based on the impedance variation e.g. by setting the threshold 34 to agree with the anticipated magnitude of the impedance variation of lung movements.

The wristwatch 102 may e.g. have the measurement unit 1 in the case and electrodes 2 in the strap. The wristwatch 102 may e.g. be configured to capture a cardiac signal by placing the electrodes 2 such that the bio-impedance between the two electrodes changes with the heart beat modulation of the blood flow in the veins of the wrist. The measurement unit 1 may be configured to output a cardiac signal based on the impedance variation e.g. by setting the threshold 34 to agree with the anticipated magnitude of the impedance variation of the heart beat modulation of the blood flow. It should be understood that respiration signals may be acquired in many different ways, not necessarily only from health patches 100. It should be understood that cardiac signals may be acquired in many different ways, not necessarily only from wrist watches 102. For example, a cardiac signal may also be acquired from a health patch 100.

In the above, the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A measurement unit for measuring a bio-impedance of a body, the measurement unit comprising a current generator circuit, a readout circuit, and a baseline cancellation current circuit,     wherein the current generator circuit is configured to amplify a reference current to form a measurement current to be driven through a body tissue of the body, such that a measurement voltage is generated, the measurement voltage depending on the measurement current and the bio-impedance of the body;

wherein the readout circuit comprises an Instrumentation Amplifier (IA) which has a transconductance stage and a transimpedance stage, wherein the IA is configured to:
produce a first current in the transconductance stage, the first current being proportional to the measurement voltage,
receive a second current from the baseline cancellation current circuit,
produce an output voltage in the transimpedance stage, the output voltage being proportional to a difference between the first current and the second current and representative of the measured bio-impedance;
wherein the baseline cancellation current circuit is configured to amplify the reference current by a factor to form the second current and deliver it to the IA,
wherein the factor is such that an absolute value of the difference between the first and the second current is below a threshold during the measurement of the bio-impedance, such that a baseline of the first current is cancelled by the second current.

2. The measurement unit of claim 1, the measurement unit being further configured to dynamically determine the factor by measuring the difference between the first and the second current.

3. The measurement unit of claim 1, wherein the threshold is based on an anticipated variation in bio-impedance.

4. The measurement unit of claim 3, wherein the anticipated variation in bio-impedance is a variation caused by respiration or heart beats.

5. The measurement unit of claim 1, wherein the baseline cancellation current circuit comprises a digital controller and a baseline cancellation current digital-to-analog converter (IDAC) (44),
wherein the digital controller is configured to measure the difference between the first and the second current; calculate the factor based on the difference between the first and the second current; and deliver a factor signal, the factor signal being a signal representation of the factor,
wherein the baseline cancellation IDAC is configured to receive the factor signal and the reference current and output the second current as the reference current multiplied by the factor.

6. The measurement unit of claim 1, the measurement unit further comprising a first and a second body tissue electrode which are configured to provide an electric connection to the body at a first and a second position respectively,
wherein the measurement unit is further configured to drive the measurement current through the body tissue between the first and second positions.

7. The measurement unit of claim 6, wherein the measurement unit is further configured to acquire the measurement voltage as a voltage between the first and the second body tissue electrode.

8. The measurement unit of claim 6, the measurement unit further comprising a third and a fourth body tissue electrode which are configured to provide an electric connection to the body at a third and a fourth position respectively,
wherein the measurement unit is further configured to acquire the measurement voltage as a voltage between the third and the fourth positions.

9. The measurement unit of claim 1, the measurement unit being further configured to extract a baseline impedance from the factor, the baseline impedance representing a time invariant impedance of the body.

10. The measurement unit of claim 1, the measurement unit being further configured to extract an impedance variation from the output voltage, the impedance variation representing a time variant impedance of the body.

11. The measurement unit of claim 10, wherein the measurement unit is further configured to output a respiration signal based on the impedance variation.

12. The measurement unit of claim 10, wherein the measurement unit is further configured to output a cardiac signal based on the impedance variation.

13. The measurement unit of claim 1, wherein the measurement unit further comprises:
a first current modulator which is configured to modulate the first current at a frequency, and
a second current modulator which is configured to modulate the second current at the same frequency as the first current modulator, such that the modulation of the first current and the second current becomes synchronized.

14. The measurement unit of claim 1, wherein the IA is configured to have a gain above 100 VN.

15. A biosignal measuring device comprising the measurement unit of claim 1.

* * * * *